US008505748B2

(12) United States Patent
Jones et al.

(10) Patent No.: US 8,505,748 B2
(45) Date of Patent: Aug. 13, 2013

(54) APPARATUS CONFIGURED TO SUPPORT SURGICAL INSTRUMENTS

(76) Inventors: Sylvia Jones, Wilmington, DE (US); Michele Lamercie Hall, Kennett Square, PA (US)

(*) Notice: Subject to any disclaimer, the term of this patent is extended or adjusted under 35 U.S.C. 154(b) by 204 days.

(21) Appl. No.: 12/662,095

(22) Filed: Mar. 31, 2010

(65) Prior Publication Data
US 2011/0240577 A1 Oct. 6, 2011

(51) Int. Cl.
*A47F 7/00* (2006.01)
*B65D 83/00* (2006.01)

(52) U.S. Cl.
USPC .................................. 211/85.13; 206/370

(58) Field of Classification Search
USPC ............. 211/65, 69.1, 69.2, 70.3, 70.6, 70.7, 211/85.13; 206/363, 370, 373, 557, 63.3
See application file for complete search history.

(56) References Cited

U.S. PATENT DOCUMENTS

| | | | | |
|---|---|---|---|---|
| D170,798 | S | * | 11/1953 | Dundon et al. ............... D15/140 |
| 3,819,039 | A | * | 6/1974 | Erickson ....................... 206/388 |
| 4,011,944 | A | * | 3/1977 | Cooley et al. ................. 206/557 |
| 4,046,254 | A | | 9/1977 | Kramer |
| 4,135,868 | A | * | 1/1979 | Schainholz ................... 422/310 |
| 4,415,089 | A | * | 11/1983 | Ruffa ......................... 211/85.13 |
| D276,462 | S | * | 11/1984 | Villarreal ...................... D24/229 |
| 4,501,363 | A | | 2/1985 | Isbey, Jr. |
| D306,481 | S | * | 3/1990 | Lang ............................. D24/133 |
| 5,046,624 | A | * | 9/1991 | Murphy et al. .............. 211/70.6 |
| D321,249 | S | * | 10/1991 | Gorski ......................... D24/229 |
| 5,082,111 | A | | 1/1992 | Corbitt, Jr. |
| 5,097,963 | A | | 3/1992 | Chernosky |
| 5,170,804 | A | * | 12/1992 | Glassman ..................... 128/849 |
| 5,195,538 | A | | 3/1993 | Eldridge, Jr. |
| 5,201,430 | A | * | 4/1993 | Artzer .......................... 211/70.6 |
| 5,207,703 | A | * | 5/1993 | Jain .............................. 606/232 |
| 5,381,896 | A | | 1/1995 | Simons |
| 5,492,671 | A | * | 2/1996 | Krafft ............................. 422/26 |
| 5,681,539 | A | * | 10/1997 | Riley ............................. 422/300 |
| 5,759,502 | A | * | 6/1998 | Spencer et al. ............... 422/300 |
| 5,779,053 | A | * | 7/1998 | Partika et al. ................. 206/570 |
| 5,848,693 | A | | 12/1998 | Davis |
| 6,193,932 | B1 | * | 2/2001 | Wu et al. ........................ 422/28 |
| D438,634 | S | * | 3/2001 | Merry ........................... D24/227 |
| 6,230,888 | B1 | * | 5/2001 | Frieze et al. .................. 206/370 |
| 6,244,447 | B1 | * | 6/2001 | Frieze et al. ............... 211/85.13 |
| 6,367,637 | B1 | * | 4/2002 | Davis et al. ................. 211/85.13 |
| 6,426,041 | B1 | * | 7/2002 | Smith ............................. 422/28 |
| 6,915,912 | B2 | * | 7/2005 | Davis et al. ................. 211/85.13 |
| 6,969,498 | B1 | | 11/2005 | Riley |
| 7,066,328 | B2 | * | 6/2006 | Pulsifer ......................... 206/363 |
| D535,753 | S | * | 1/2007 | Bennison ...................... D24/217 |
| D535,754 | S | * | 1/2007 | Bennison ...................... D24/217 |
| 7,303,568 | B2 | * | 12/2007 | Jannot ........................... 606/148 |
| 8,069,998 | B2 | * | 12/2011 | Thomas ..................... 211/85.13 |
| 2006/0076254 | A1 | * | 4/2006 | Corbitt et al. ................. 206/370 |
| 2009/0146026 | A1 | * | 6/2009 | Dredla, IV ................... 248/163.1 |

* cited by examiner

*Primary Examiner* — Jonathan Liu
*Assistant Examiner* — Joshua Rodden
(74) *Attorney, Agent, or Firm* — Emdadi Patent Law; Kamran Emdadi

(57) ABSTRACT

An apparatus to support various surgical instruments is disclosed. The apparatus may include numerous chambers that may be used to separate different instruments. The chambers may have grooves that are used to support the instruments, and the height of the apparatus from the supporting surface may be comparable to the measurements of the instruments to provide a securing surface.

3 Claims, 6 Drawing Sheets

TOP/
SIDEWAYS
PERSPECTIVE

FRONT VIEW
OF CHAMBER

REAR VIEW
OF CHAMBER

SIDEWAYS
PERSPECTIVE

SIDEWAYS
PERSPECTIVE

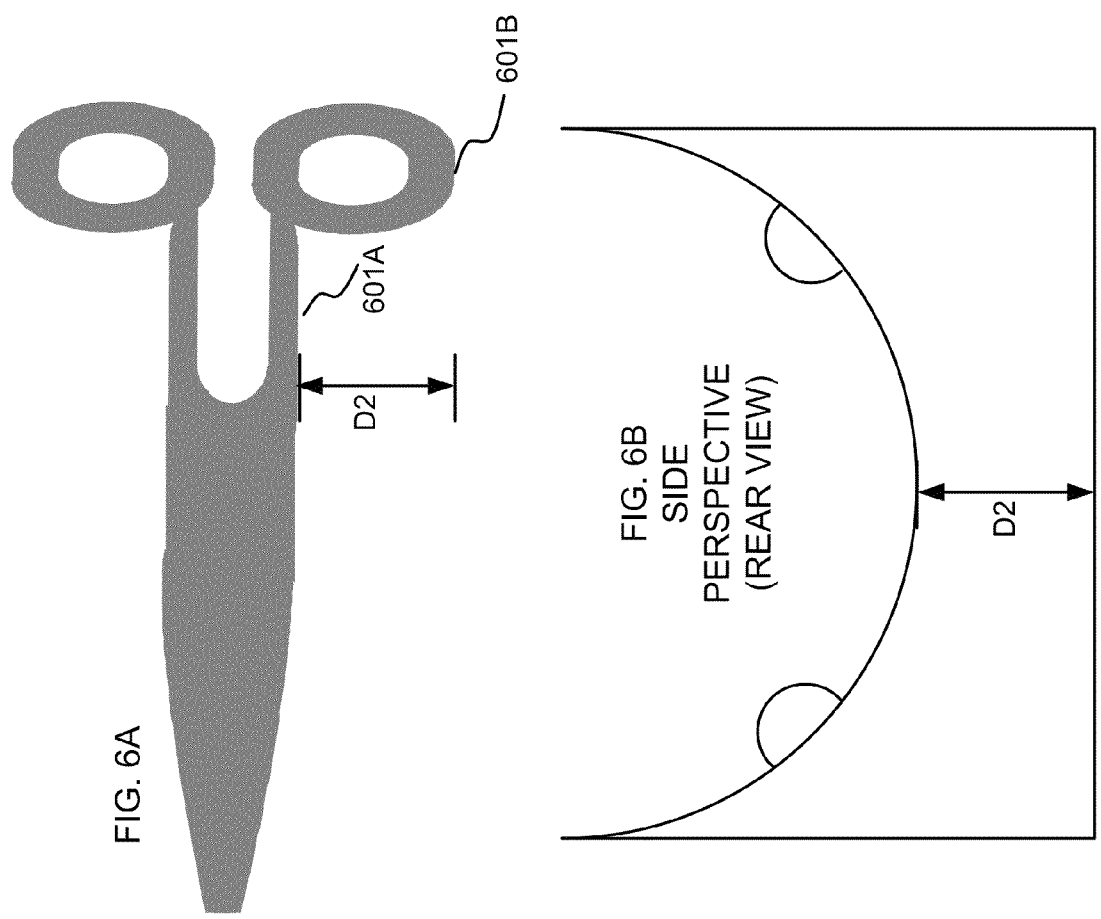

APPARATUS CONFIGURED TO SUPPORT SURGICAL INSTRUMENTS

TECHNICAL FIELD OF THE INVENTION

This invention relates to an apparatus configured to support various surgical instruments during a surgical operation.

BACKGROUND OF THE INVENTION

Medical surgeries have always been performed in an operating room ("OR"). The protocol for preparing a surgeon and his or her surgical team requires the utmost care and diligence to avoid infection to the patient. Conventionally, surgical instruments, such as, clamps, retractors, forceps, suture ties, containers, and towels, are all sterile and carefully introduced onto the sterile field of the OR.

Historically, the items that may be brought into an OR are limited by the slowly changing field of surgery in general. Over time, the surgical instruments have evolved to include various different shapes and materials, however, for the majority of surgical items, very little has changed over the years. One such item that is used frequently in almost all surgical procedures and setups is the lint free towel. Such towels must be lint free so as to avoid introducing towel fibers into the patient's body which may be exposed and vulnerable during a surgical procedure, increasing the likelihood of infection.

The lint free towels are made of a material which does not roll-off lint as a result of being used to soak fluids or wipe hands. In addition, the lint free towels are sterilized and are ready for surgery when delivered. The lint free towels are used in abundance and may be one of the most commonly used items in the OR. For example, in any given OR, there may be lint-free towels setup for the surgeon to wipe his or her hands, and there may be lint free towels on the floor to collect fluids which may have fallen off the operating table. In addition, there may be lint free towels on the mayo stand providing a cushion and a barrier over an impervious cover drape for the mayo stand. Lint free towels provide an artificial mold used to organize the many surgical instruments which will be used during a surgical operation.

One example of a conventional OR setup may include two or more towels draped across the mayo stand to create a lip used to expose suture ties placed under the lip of the towel, which may be labeled by a surgical technician. Additional towels may be bunched together to create grooves used to separate the many numerous surgical instruments, as illustrated in FIG. 1. Towels each cost several dollars and have been adding unnecessary expenses to the hospital, patient and insurance companies for years, especially when they are used in ways that a simpler and more affordable device would provide a faster and more effective alternative.

SUMMARY OF THE INVENTION

An example embodiment of the present invention may include an apparatus configured to support a plurality of surgical instruments. The apparatus may include a plurality of concave chambers, which include a plurality of supporting grooves. The apparatus may also include a first low point of the concave chambers that is lower than a second low point of the concave chambers with respect to the resting surface of the apparatus.

BRIEF DESCRIPTION OF THE DRAWINGS

FIGS. 6A and 6B illustrate examples of the height of the surgical instrument and a low point of the bracket chamber at the position it is laid across the bracket.

DETAILED DESCRIPTION OF THE INVENTION

It will be readily understood that the components of the present invention, as generally described and illustrated in the figures herein, may be arranged and designed in a wide variety of different configurations. Thus, the following detailed description of the embodiments of an apparatus, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present invention. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

Figure 1:
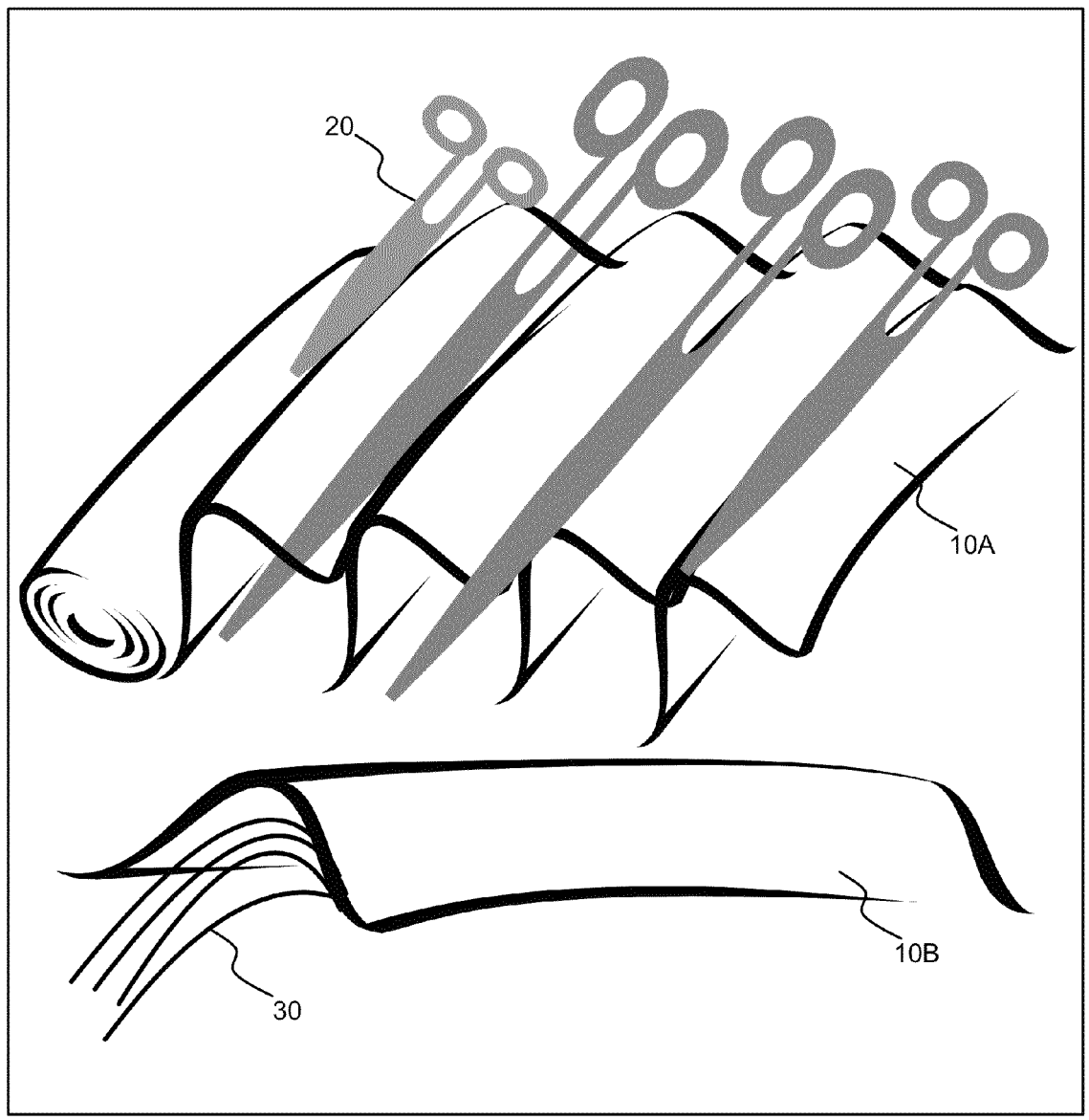
FIG. 1 illustrates a conventional towel arrangement used to organize surgical tools and suture ties.

FIG. 1 illustrates conventional uses of a lint free surgical towel. Referring to FIG. 1, a first towel 10A is illustrated as having been bunched together by a surgical technician in an effort to provide grooves which may hold surgical instruments 20 upright or semi-upright and may separate the different types of instruments for easy access by the technician. Such a configuration requires time and effort to make the instruments stay in place. The extra towel is also used as a prop and not for its intended purpose, which is to soak fluids or provide a barrier to reduce the likelihood of contamination. The towel in this illustration may be on top of a mayo stand.

The lower part of FIG. 1 illustrates another towel 10B being used to create a lip and/or passage for suture ties 30 to be laid onto the mayo stand. Also, an additional towel (not shown) may be laid across the towel 10B to create a first layer that the lip may be formed over. None of these towels 10A and/or 10B are being used to soak fluid, and may therefore be replaced by other materials and/or devices to save time and costs associated with a surgical procedure.

Figure 2A:
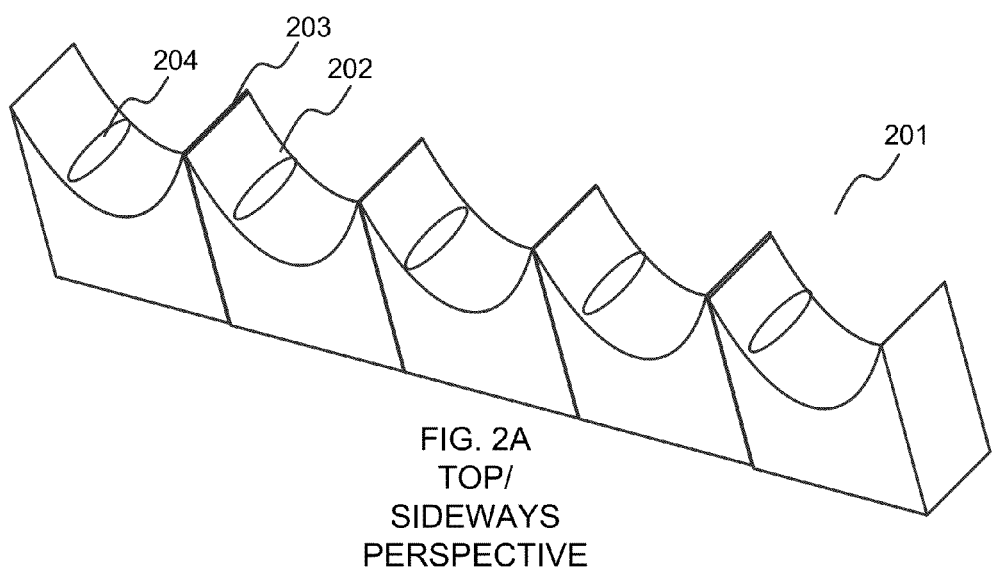
FIG. 2A illustrates an example bracket used to hold surgical instruments, according to example embodiments of the present invention.

FIG. 2A illustrates an example holding bracket, according to example embodiments of the present invention. Referring to FIG. 2A, a bracket 201 includes five chambers 202, which may further include any number of grooves 204, and which may further include spacers 203. The grooves may be indentations from an underside perspective of the medical instrument holding device. Or, alternatively, from a top perspective, the grooves may instead be viewed as protrusions extending outward from a surface area of the chambers 202. For purposes of this disclosure, the terms "protrusion" and "groove" may be used interchangeably. The number of chambers 202 per bracket 201 may range from two to twelve or more depending on the preference of the OR personnel and/or the surgical procedure being performed. The spacers 203 may represent the end of one chamber and the beginning of a new chamber 202. The spacers may be relatively small in width and/or may be as large as one inch or more. The spacers may be rounded and smooth to the touch, or, may be cut precisely to have a fine edge to avoid wasting excess materials.

During a surgical operation, any number of surgical instruments may be positioned in the chambers 202 of the bracket 201. One example configuration may include placing similar instruments in the same chamber 202 and using the different chambers to hold different instruments. There is no limit on the number of instruments that may be placed in a single chamber 202, however, provided that the instruments are positioned securely and/or semi-upright and are accessible by the surgical technician.

Figure 2B:
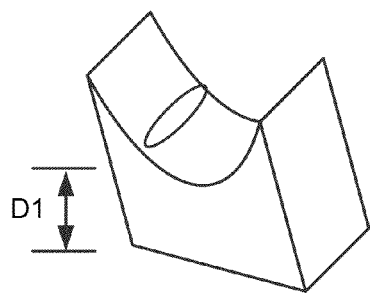
FIGS. 2B and 2C illustrate front and rear views of the individual chambers within a bracket.
Figure 2C:
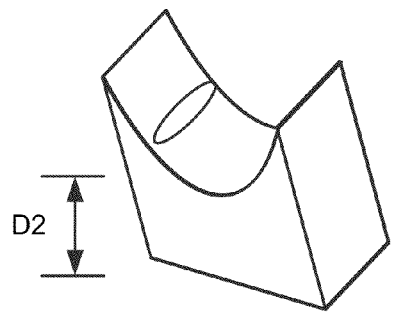

FIGS. 2B and 2C illustrate examples of the front and rear views of a single chamber 202. In this example, the low point of the curve of the surface of the chambers may vary in height from the front of the chamber to the rear of the chamber (D1 vs. D2). The height of the rear portion (D2) should be greater than the height of the front portion (D1) to provide the proper angle and gravitational force to support a surgical instrument. Although the illustrations are not drawn to scale, the difference in height should be between ⅛ inch and ½ inch. The height of D2 should be approximately the distance from the surgical instrument base to the exterior surface of the surgical instrument finger holder (as discussed in detail with reference to FIG. 6). This provides a way to allow the surgical instrument to touch the surface of the table at more than one place. In one example D2 is one inch and D1 is ½ inch. In another example, D2 is ¾ inch and D1 is still ½ inch.

The grooves 204 may vary in number and size. As illustrated in FIG. 2A, the grooves may be formed inside the chambers 202 and may include two grooves per chamber. Alternatively, the grooves 204 may vary in size and quantity, and may be as low as two per chamber and as many as a hundred per chamber. The grooves 204 may be formed from the same material as the bracket 201, or, alternatively, the grooves may be a different material than the bracket 201.

Figure 3A:
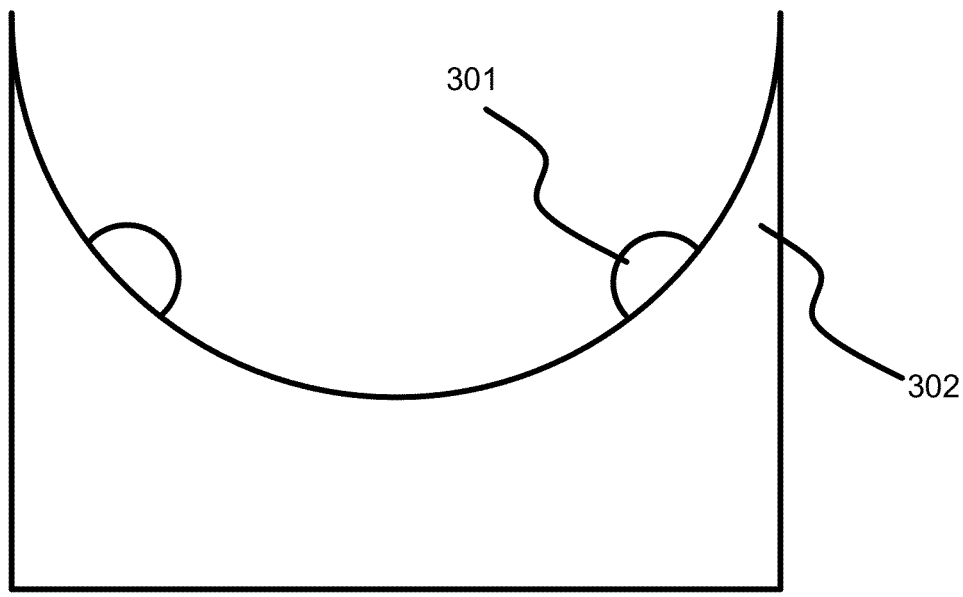
FIGS. 3A and 3B illustrate a sideways perspective of a chamber.
Figure 3B:
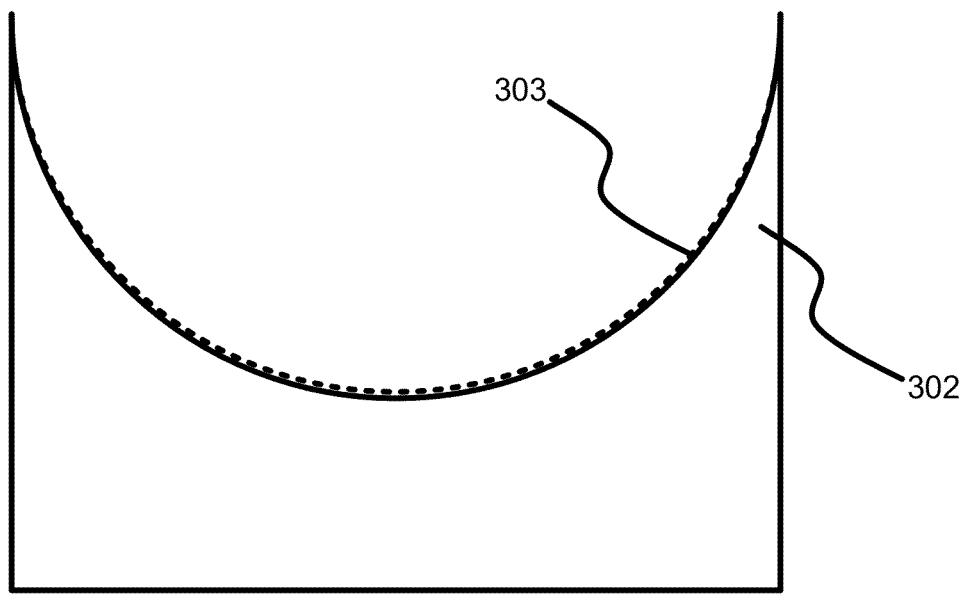

Instead of grooves, the inside of the chambers 202 may have a gripping surface, such as, gripping tape or a scored, rough surface, as illustrated in FIG. 3B. Such a rough surface 303 would provide a non-slipping surface for the surgical instruments to stay in a substantially up-right position.

FIG. 3A illustrates a sideways perspective of a chamber, according to example embodiments of the present invention. Referring to FIG. 3A, a chamber 302 includes two grooves 301, which may be used to support the surgical instruments during a surgical operation. As noted above, the number of grooves may vary (i.e., two, four, etc.) and may be replaced by other forms of non-slipping material.

Figure 4:
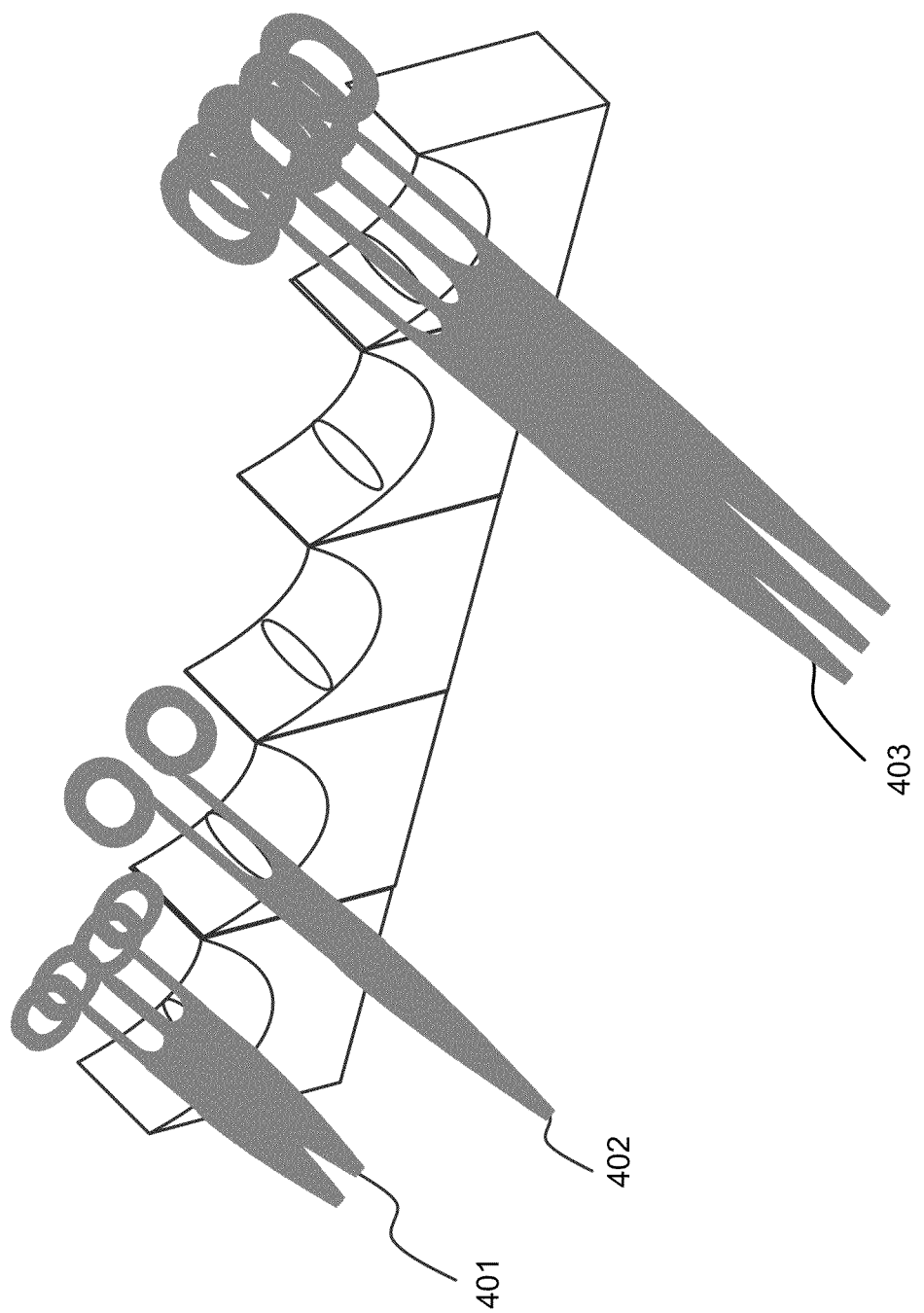
FIG. 4 illustrates the example bracket of FIG. 2A in use with surgical instruments being held, according to example embodiments of the present invention.

FIG. 4 illustrates the bracket being used to support surgical instruments. The surgical instruments may include, for example, needle holders, Kellys, hemostats, towel clips, sponge sticks, Mayo scissors, Metz scissors, Kocher clamps, right angle clamps, etc. All of these instruments vary in length and purpose, however, most of these instruments have a distance of ¾ inch to 1 inch from the base to the outside extremity of the finger socket (as discussed in FIG. 6A).

FIG. 4 illustrates three different surgical instruments 401-403 and a total of six instruments being securely positioned in a single chamber. In this example, like instruments are placed in common chambers. Additional instruments may be placed in a single chamber depending on the type of surgical operation. The distance of the chamber may be as short as four inches and as long as fourteen inches. The number of chambers may vary depending on the total length of the chamber.

The bracket may be approximately one inch in width. The number of chambers in the bracket may vary according to length. For example, a 10 inch bracket may hold 0-12 instruments and may be have 5-10 chambers. In another example, a bracket may be 14 inches long and may hold additional instruments. In another example embodiment, the number of chambers and the length of the bracket may be adjustable by a sliding mechanism that allows the bracket to be expanded by sliding one side of the bracket out from the other side to adjust the total number of chambers and the overall size of the bracket.

The bracket may also be secured to the mayo stand or other surface via an adhesive tape that is on the bottom of the bracket. The material of the bracket may be plastic or a low cost material that is easily mass produced. The bracket may be disposable and/or may be cleaned and sterilized for additional uses.

Figure 5:
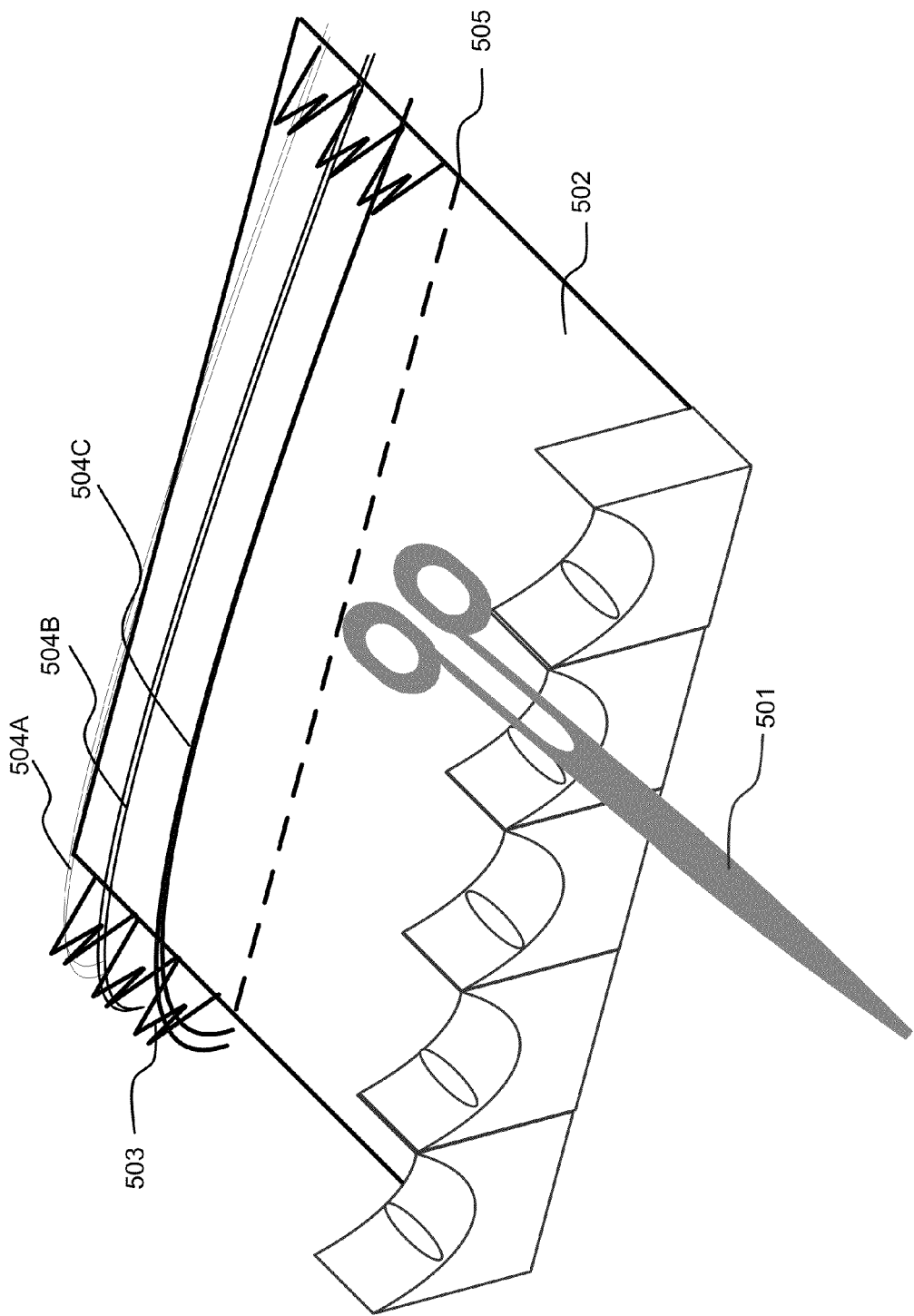
FIG. 5 illustrates another example embodiment used to hold suture ties in addition to the bracket.

FIG. 5 illustrates another example embodiment of the present invention. Referring to FIG. 5, a suture tie rack 502 may be part of the bracket. For instance, the suture tie rack 502 may be a substantially flat surface that is molded or created as part of the bracket during a manufacturing process of molding the bracket.

The suture tie rack 502 may have a breakable edge 505 that may be bent and snapped-off of the portion of the suture tie rack that is attached to the bracket. The suture tie rack has a plurality of slits formed in each pair of suture tie holders 503, which conveniently hold suture ties laid into position across the suture tie holders 503. The suture ties 504A, 504B and 504C may be different sizes (gauges) and may need to be organized and separated at the start of a surgical operation. As illustrated in FIG. 5, the surgical instrument 501 is free from obstruction and is not affected by the suture ties 504A, 504B and/or 504C, which are laid above the area of the chambers.

FIG. 6A illustrates an example measurement of a surgical instrument from its base 601A to the outer portion of the finger socket 601B. During a surgical procedure, the surgical instrument would be placed in the chamber and the outer portion of the finger socket 601B would make contact with the table to provide additional support for the instrument. The distance D2 would preferably be between ¾ inch and 1 inch as most instruments have a comparable distance.

FIG. 6B illustrates the distance D2 being implemented on the rear side of the chamber of the bracket. The surgical instrument would then make contact with the table at the finger socket portion of the instrument. As noted previously, the front side of the bracket and its corresponding chamber would preferably be somewhat smaller than the distance of the rear side of the bracket. The variation in distance from the front side of the bracket to the rear side may be as small as 1/16 of an inch to as large as ½ of an inch to provide support for the weight of the surgical instrument.

While preferred embodiments of the present invention have been described, it is to be understood that the embodiments described are illustrative only and the scope of the invention is to be defined solely by the appended claims when considered with a full range of equivalents and modifications (e.g., protocols, hardware devices, software platforms etc.) thereto.

What is claimed is:

1. An apparatus configured to support a plurality of surgical instruments, the apparatus comprising:
a plurality of spacers; and
a plurality of concave chambers each of which has a uniform width distance as measured between two of the spacers, wherein a length and width of each of the plurality of spacers is smaller than a distance across each of the plurality of concave chambers, and wherein each individual spacer is positioned at a top portion between two separate concave chambers of the plurality of concave chambers, and wherein each of the plurality of concave chambers include:
two supporting protrusions positioned only on sidewall portions of each of the concave chambers above a lower portion of the concave chambers with one supporting protrusion of the two supporting protrusions positioned on one sidewall of each of the respective concave chambers and the other one of the two supporting protrusions positioned on a second sidewall of each of the respective concave chambers, and wherein a surface area of each of the two supporting protrusions includes a semicircular shape extending from a first higher position of each of the respective sidewalls to a lower second position of each of the respective sidewalls, and
wherein a lowest point of a bottom surface of each of the plurality of concave chambers comprises a sloped surface wherein a first low point of the sloped surface is on a front side of the apparatus and a second low point of the sloped surface is on a rear side of the apparatus, the first low point being closer in distance to a resting surface supporting the apparatus than a distance between the resting surface and the second low point; a suture tie rack configured with a plurality of suture tie holders, wherein the suture tie rack includes a breakable edge such that the suture tie rack may be removed from the apparatus.

2. The apparatus of claim 1, wherein a distance of the first low point measured from a bottom of the apparatus is approximately ½ inch and a distance of the second low point measured from the bottom of the apparatus is approximately 1 inch.

3. The apparatus of claim 1, wherein the apparatus is entirely one material.

* * * * *